United States Patent [19]
Davis

[11] Patent Number: 5,352,181
[45] Date of Patent: Oct. 4, 1994

[54] METHOD AND RECORDING FOR PRODUCING SOUNDS AND MESSAGES TO ACHIEVE ALPHA AND THETA BRAINWAVE STATES AND POSITIVE EMOTIONAL STATES IN HUMANS

[76] Inventor: Mark E. Davis, 24902 Oak Creek, Lake Forest, Calif. 92630

[21] Appl. No.: 939,088

[22] Filed: Sep. 2, 1992

[51] Int. Cl.⁵ .......................................... A61M 21/00
[52] U.S. Cl. ...................................................... 600/28
[58] Field of Search ...................................... 600/26–28; 128/731–732, 897–898; 84/611–612, 635–636, 651–652, 667–668, 713–714

[56] References Cited

U.S. PATENT DOCUMENTS

| | | | |
|---|---|---|---|
| 3,060,795 | 10/1962 | Corrigan et al. | 88/16.6 |
| 3,278,676 | 10/1966 | Corrigan et al. | 178/6 |
| 4,141,344 | 2/1979 | Barbara | 600/28 |
| 4,227,516 | 10/1980 | Meland et al. | 600/26 |
| 4,395,600 | 7/1983 | Lundy et al. | 179/1.5 M |
| 4,777,529 | 10/1988 | Schultz et al. | 358/143 |
| 5,123,899 | 6/1992 | Gall | 600/28 |
| 5,128,765 | 7/1992 | Dingwall et al. | 358/182 |
| 5,135,468 | 8/1992 | Meissner | 600/28 |
| 5,151,080 | 9/1992 | Bick | 600/26 X |

OTHER PUBLICATIONS

Ostrander & Schroeder, *Super-Learning*, Feb. 1981, pp. 49, 64, 68–69, 114–115, 312–315.
Prevention Magazine, Healthy Pleasures, Jun. 1989, pp. 97–101.
Fast Track Magazine, See Me, Feel Me, Touch Me, Heal Me, Feb. 1991, p. 26.
American Journal of Nursing, Forty-five Minutes of Mozart, BID, Feb. 1992, p. 13.
Journal of American Medical Assoc., Medical News and Perspectives, Music Aids Elderly, Sep. 1991, pp. 1323–1329.
Moss & Webster, Nations Business Magazine, Music & Wellness, May, 1986, p. 1.

*Primary Examiner*—Angela D. Sykes
*Attorney, Agent, or Firm*—Walter A. Hackler

[57] ABSTRACT

A method and recording for use in achieving Alpha and Theta brain wave states and effecting positive emotional states in humans to enhance learning and self-improvement, is provided which includes a medium having a musical composition recorded thereon with an initial tempo decreasing to a final tempo and verbal phrases, comprising between approximately 4 and approximately 8 words, recorded in synchrony with the decreasing initial tempo.

10 Claims, 1 Drawing Sheet

METHOD AND RECORDING FOR PRODUCING SOUNDS AND MESSAGES TO ACHIEVE ALPHA AND THETA BRAINWAVE STATES AND POSITIVE EMOTIONAL STATES IN HUMANS

BACKGROUND

1. Field of the Invention

This invention relates to a method for producing sounds (musical/instrumental) and messages (words and phrases) to achieve specific conscious brainwave states (Alpha and Theta), and positive emotional states (peace, comfort, well-being, confidence, and relaxation), which brainwave and emotional states are conducive to heightened and accelerated absorption for learning, greater receptivity to creativity, confidence and self-esteem, as well as the enhancement of self-image, and the overall physical and emotional health in humans.

2. Discussion of Prior Art

A prior art search was conducted by the following means:

(1) a formal search (using the firm of Prior Art Searches, Inc.) related to all sound/message systems and methods; and (2) a thorough search of publications related to all sound/messages systems and methods.

The search revealed certain types of sound/message methods and systems in the form of audio or audio/-visual tape recordings which were created and produced to influence individuals, by the promotion of products (i.e., self improvement recordings, having themes such as non-smoking, exercise, relaxation, positive thinking, motivation, etc.)

No prior art was revealed in the patents cited herein that reveal any effort towards a patentable invention that provides an audible sound/message method for the specific purpose to (1) achieve the Alpha and Theta brainwave states; and to (2) achieve positive emotional states, in humans.

The cited publications relate to and support this invention. The cited publications relate to and support the inventions' theory that certain types of sound/message methods produce states of consciousness in humans that enhance listening, learning, instilling feelings of comfort, security, and safety. The Alpha and Theta brainwave states, therefore, are the catalyst for a healthy and happy life.

Although there have been discussions and publications regarding the correlation of learning to particular brainwave states in the last thirty years, surprisingly, little development has been accomplished within this particular scope of the art and its knowledge.

The prior art search, therefore, was directed towards inventions having sound/message systems and/or methods that specifically attempt to achieve, for any reason, particular brainwave and emotional states in humans.

The closest prior art revealed in the search and which are referenced in the attached Form 1449, are U.S. Pat. Nos. 3,060,795; 3,278,676, 4,395,600; 4,777,529; and 5,128,765, which all relate generally to systems and methods for producing auditory or auditory/visual subliminal messages adapted for use in self-improvement programs, anti-shoplifting messages in shopping centers, etc. All are indirectly relate d to brainwave states, but are focused on the use of subliminal, inaudible (unconscious) messages, rather than the conscious present inventions' audible, conscious presentation of material (not subliminal) to achieve the receptive Alpha and Theta brainwave states and then direct audible messages in a far superior way to heighten the absorption of verbal material by the human mind.

To the inventor's knowledge, prior art (patented or published) does not reveal the true, novel concepts of his particular invention.

None of the prior art has dealt with the actual systematic coordination of using gentle musical instrumentation and messages at specific gravitating tempos to achieve the Alpha and Theta brainwave states, which states are conducive to receptivity to learning, building confidence, self-improvement, relaxation and stress reduction, a sense of calm, well being, security and comfort, and self-esteem. In pace with these tempos, positive phrases are specifically placed over the instrumentation.

In the present invention, sounds (instrumentation) are used which induce Alpha nd Theta brainwave states and messages (words and phrase) are used which penetrate more deeply into the mind for long-term benefits. Here, the gentle instrumentation and tempos achieve a relaxed and receptive state in the listener which state is conducive to the receptivity of the positive phrases then spoken and an overall enhancement of learning.

OBJECTS AND ADVANTAGES

Several objects and advantages of the present invention are, generally, to provide a method for producing tape recordings using loving words and phrases (messages) gently spoken over calming music (sounds) using certain instruments and specific tempos to achieve Alpha and Theta brainwave states in individuals in order to:

(a) enhance listening and learning;

(b) relax, soothe and provide feelings of comfort, security and feelings of well-being;

(c) encourage growth and health;

(d) reduce stress;

(e) build confidence, and offset negativity;

(f) inspire a productive, happy life;

(g) improve intuition and creativity;

(h) create positive attitudes/outlooks; and (i) renew hopefulness and optimism in humans.

The present invention is made up of the following components/methods:

(1) An original musical composition is instrumentalized with soft, low-dynamic range instruments, such as strings, bells, and voices, having tempos of the composition purposefully gravitating from approximately 65–120 beats per minute, slowly descending to approximately 40–60 beats per minute.

It is widely known in the art that certain brainwave states (BWS)(brainwave cycles per second) are achieved by maintaining certain tempos throughout a musical composition and/or presentation of message materials. Generally, musical compositions having "slow, monotonous rhythm, a non-distracting melodic structure (not the hum-along kind), and harmonic patterns based on specific ratios". Gives the best results in which Alpha and Theta brainwaves are achieved.

The correlation of tempos (beats per minute) to brainwave cycles per minute can be summarized as follows:

| Composition and/or Scripts' Tempo/Beats Per Minute | Brainwave Cycles Per Minute | Brainwave State Achieved |
| --- | --- | --- |
| 70+ | 13–25 | Beta |
| 60 | 8–12 | Alpha |
| 50 | 4–7 | Theta |
| 40 | 1–4 | Delta |

While studies show music of 60 beats per minute inducing the highly creative Alpha state, the object of reducing the beats per minute throughout the composition is intended to gradually achieve a human's Alpha and Theta brainwave states (or frequencies), which brainwave states are even more conducive to learning and absorption of audible materials, such as in hypnosis when accelerated learning occurs on the way down to Theta. As supported in the discussions in *Super Learning,* in the Disclosure Statement, the brains' brainwave cycles or rhythms try to match or synchronize the rhythm or tempos of sounds and/or messages. In the present invention, the utilization of specific sound/message rhythms (tempos) induce human brainwaves to match or synchronize themselves to such sound/message rhythms (tempos).

As an example, sound/message systems recorded with rhythms (tempos) set at approximately 70+ beats per minute will induce the brain's brainwave cycles per second to match or synchronize to those rhythms, producing the Beta brainwave state (frequency) in humans. This particular brainwave state produces feelings of, excitement, tension and stress. Unlike the Alpha and Theta brainwave state, the Beta brainwave state is not conducive to relaxation, concentration and learning.

(2) A script is developed which is centered around a central theme such as learning, self-esteem, appreciation for health, feelings of joy and well-being. The words are scripted with approximately 4–8 words per phrase, with pauses inserted between phrases of approximately 4–8 seconds between phrases. The words and phrases of the script are paced to the descending tempo (beats per minute) of the musical composition.

The object of the specific number of words per phrase, the pauses between phrases, the word speed within the phrases, and the pacing of the words with the descending beats per minute in the musical composition, is intended to have the brains' cycles match and synchronize to achieve the Alpha Theta brainwave states, causing a high degree of receptivity.

The present invention uses musical compositions and scripts, having specific tempos or rhythms to induce a certain relaxation level in humans or to evoke a specific psycho-physical state of relaxed concentration. By reducing an individual's brainwave state to the Alpha and Theta (relaxation) levels, the individual is sufficiently relaxed for accelerated learning to occur. The mind achieves a restful alertness, wherein concentration is at its best.

DRAWING FIGURES

Reference Numbers in Drawings
12 Composition
14 Keyboard
16 8-Track Recorder
22 Script
26 Adjustments
28 Master Tape (final product)

DESCRIPTION OF FIGURES—FIGS. 1 TO 3

Figure 1:
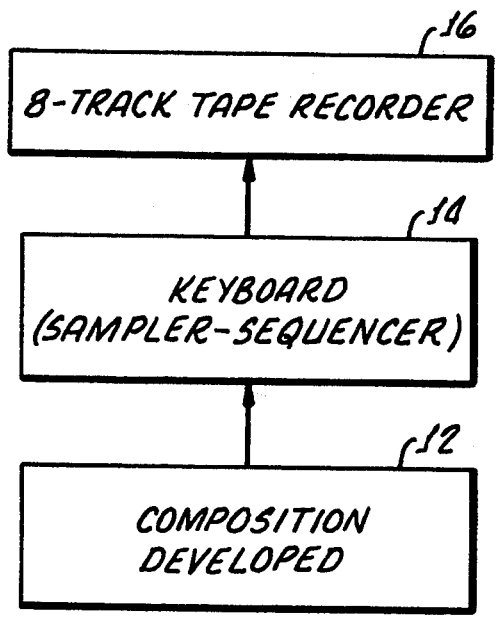
FIG. 1 is a diagram of the various components in the development of the sound (instrumentation) system.

Referring to FIG. 1, the various components of the sound (instrumentation) method are presented. An original musical Composition 12, is developed and instrumentalized in soft, low-dynamic range instruments, (i.e. strings, bells, voices). The Composition 12 is then performed on a standard, 16-track, digitalized Keyboard 14, with sampler and sequencer. The resulting instrumentation is then fed into a standard 8-Track recorder 16, on 2 of its 8 tracks. The Keyboard 14 is manually adjusted while being fed into 8-Track Recorder 16, taking the tempo of approximately 60–120 beats per minute, then, by manual adjustment, descending to approximately to 40–60 beats per minute, at regular intervals over the length of the Composition 12. The resulting slow descent in the beats per minute tempo is virtually imperceptible, occurring at approximately 2 beats, descending the tempo per minute for each composition.

Figure 2:
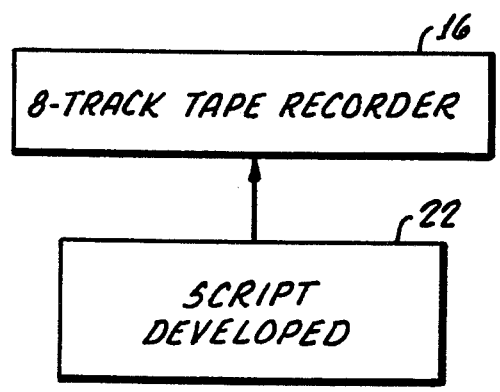
FIG. 2 is a diagram of the various components in the development of the message (words and phrases) system.

Referring to FIG. 2, the various components of the message (words and phrases) method are presented. Script 22 is developed around a central theme (e.g., learning, self-esteem, growing healthy, etc.), using approximately 4–8 words per phrase, with pauses between phrases of approximately 4–8 seconds. Script 22's tempo must match the slowing tempo of Composition 12. Script 22 is read by human "readers" into an open microphone, in which Script 22 is fed into 8-Track Recorder 16, using 2 more of its 8 tracks.

Figure 3:
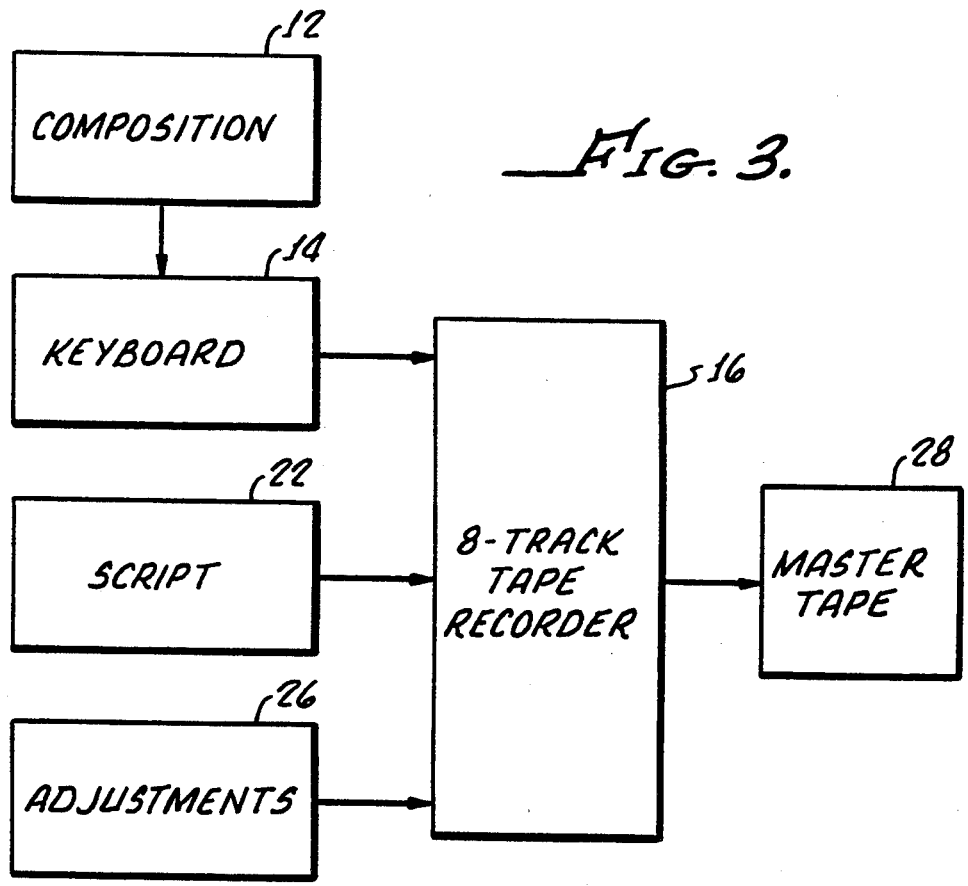
FIG. 3 is a diagram of the combined sound/message system, creating the present invention.

Referring to FIG. 3, the components of both the sound and message methods are combined and presented. In the drawing, 8-Track Recorder 16 now contains 2 tracks of instrumentation and 2 tracks of messages. The final instrumentation is then fed onto the remaining 4 tracks of 8-Track Recorder 16. This further instrumentation eliminates all harsh tones and imbalances. An 8-Track Recorder 16's tracks are then synchronized and mixed, with volume/stereo Adjustments 26, providing emphasis on the music, with volume of the messages audible, but not overbearing. A master tape 28 is then created, producing the present invention.

Scope of Invention

Although the description above contains many specificities, these should not be construed as limiting the scope of the invention but as merely providing illustrations of some of the presently preferred embodiments of this invention. For example, the present invention is presently geared for young children, but is extremely effective with adults. Tapes specifically for the benefit of adults and teenagers are under development.

Thus, the scope of the invention should be determined by the appended claims and their legal equivalents, rather than by the examples given.

The method of this invention utilizes a standard 16 track digital sampler/sequencer and a standard 8 track tape recorder/mixer. In the present invention, a KORG 01/WFD Music Workstation (16 track digital sampler/sequencer), and a TASCAM (8-track tape recorder/mixer is provided.

I claim:

1. A method for producing an audio sound tape for use in achieving Alpha and Theta brainwave states and effecting positive emotional states in humans to enhance learning and self-improvement, said method comprising:

recording on an audio tape, a musical composition having an initial tempo; and during recording of the musical composition reducing the initial tempo at regular intervals over a length of the musical composition until a final tempo is reached at an end of the musical composition, said initial tempo being reduced at a rate of approximately 2 beats per minute.

2. The method according to claim 1, wherein the musical composition is recorded at an initial tempo of between approximately 60 and approximately 120 beats per minute.

3. The method according to claim 2, wherein the musical composition is recorded to a final tempo of between approximately 40 to approximately 60 beats per minute.

4. The method according to claim 1, further comprising the step of recording on the audio tape, in synchrony with the reducing tempo of the musical composition, a plurality of verbal phrases.

5. The method according to claim 4, wherein the verbal phrases are recorded with between approximately 4 and approximately 8 words per phrase.

6. A method for producing an audio sound tape for use in achieving Alpha and Theta brainwave states and effecting positive emotional states in humans to enhance learning and self-improvement, said method comprising:

recording on an audio tape, a musical composition having an initial tempo;

during recording of the musical composition reducing the initial tempo at regular intervals over a length of the musical composition until a final tempo is reached at an end of the musical composition; and recording on the audio tape, in synchrony with the tempo of the musical composition, a plurality of verbal phrases, said verbal phrases being recorded with between approximately 4 and approximately 8 words per phrase with pauses between verbal phrases between approximately 4 seconds and approximately 8 seconds.

7. A recording for use in achieving Alpha and Theta brainwave states and effective positive emotional states in humans to enhance learning and self-improvement, said recording comprising:

a medium having a musical composition recorded thereon with an initial tempo decreasing to a final tempo with verbal phrases, comprising between approximately 4 and approximately 8 words, recorded in synchrony with the decreasing initial tempo, the initial tempo decreasing at a rate of approximately 2 beats per minute.

8. The recording according to claim 7, wherein the verbal phrases are recorded, with pauses therebetween, of between approximately 4 seconds and approximately 8 seconds.

9. The recording according to claim 8, wherein the initial tempo is between approximately 60 and approximately 120 beats per minute.

10. The recording according to claim 9, wherein the final tempo is between approximately 40 and approximately 60 beats per minute.

* * * * *